United States Patent [19]

Fremery et al.

[11] 4,359,591

[45] Nov. 16, 1982

[54] PROCESS FOR THE O-SUBSTITUTION OF PHENOLS

[75] Inventors: Max Fremery, Wesseling; Karl-Heinz Keim, Heimerzheim; Joachim Korff, Bornheim-Sechtem, all of Fed. Rep. of Germany

[73] Assignee: Union Rheinische Braunkohlen Kraftstoff Aktiengesellschaft, Wesseling, Fed. Rep. of Germany

[21] Appl. No.: 248,709

[22] Filed: Mar. 30, 1981

[30] Foreign Application Priority Data

Mar. 29, 1980 [DE] Fed. Rep. of Germany ....... 3012357
Jan. 10, 1981 [DE] Fed. Rep. of Germany ....... 3100517
Jan. 13, 1981 [DE] Fed. Rep. of Germany ....... 3100734
Feb. 5, 1981 [DE] Fed. Rep. of Germany ....... 3103839

[51] Int. Cl.$^3$ ............................................. C07C 37/11
[52] U.S. Cl. ................................... 568/804; 568/781; 568/786; 568/789; 568/790; 568/791
[58] Field of Search ............... 568/804, 789, 781, 786, 568/790, 791, 794

[56] References Cited

U.S. PATENT DOCUMENTS 2,448,942  9/1948  Winkler et al. .................... 568/804
3,953,529  4/1976  Yonemitsu et al. ................ 568/804
4,208,537  6/1980  Kawamats et al. ................ 568/804
4,227,024 10/1980  Leach ................................. 568/804

FOREIGN PATENT DOCUMENTS 2127083 12/1971 Fed. Rep. of Germany ...... 568/804
2235389  2/1973 Fed. Rep. of Germany ...... 568/790
2329812  1/1974 Fed. Rep. of Germany ...... 568/804
2547309  5/1976 Fed. Rep. of Germany ...... 568/804
7407856 12/1974 Netherlands ....................... 568/804
7512390 10/1975 Netherlands ....................... 568/804

*Primary Examiner*—Werren B. Lone
*Attorney, Agent, or Firm*—Connolly and Hutz

[57] ABSTRACT

This invention relates to a process for reacting phenol, mono- and di-alkyl phenols having at least one free o-position with methanol and/or dimethyl ether in the gas phase to form o-substituted phenols in the presence of a catalyst of oxides of iron, chromium, silicon and at least one oxide of an alkaline-earth metal, lanthanum and manganese or in the presence of a catalyst of oxides of iron, chromium, a metal from the group comprising germanium, titanium, zirconium, tin, lead, and at least one oxide of an alkali metal, alkaline-earth metal, lanthanum and manganese.

10 Claims, No Drawings

PROCESS FOR THE O-SUBSTITUTION OF PHENOLS

BACKGROUND OF THE INVENTION (1) Field of the Invention

This invention relates to a process for reacting phenol, mono- and di-alkyl phenols having at least one free o-position with methanol and/or dimethyl ether in the gas phase to form o-substituted phenols in the presence of a catalyst of oxides of iron, chromium, silicon and at least one oxide of an alkaline-earth metal, lanthanum and manganese or in the presence of a catalyst of oxides of iron, chromium, a metal from the group comprising germanium, titanium, zirconium, tin, lead, and at least one oxide of an alkali metal, alkaline-earth metal, lanthanum and manganese.

(2) Description of the Prior Art

The production of o-substituted phenols, for example 2,6-dimethyl phenol or 2,3,6-trimethyl phenol, is of considerable commercial interest because of the first of these two phenol derivatives is required for numerous applications, particularly the production of polyphenylene oxide, whilst the second derivative may be used for example as a preliminary stage in the production of vitamin E. Although synthesis processes are known from the patent literature, there has never been a process by which o-substitution products can be obtained highly selectively from phenols having free o-positions with production times that are long enough for practical application. Although phenol can be reacted to form 2,6-dimethyl phenol with a selectivity of the order of 99% in accordance with German Offenlegungsschrift No. 21 27 083, a selectivity of only 95% is obtained where o-cresol is used as the starting material.

German Offenlegungsschrift No. 19 48 607 describes a process in which o-cresol is converted into 2,6-dimethyl phenol with a selectivity of around 84%. Conversely, a selectivity of 98% is obtained with o-cresol as the starting product according to German Offenlegungsschrift No. 24 28 056. Where phenol is used, however, a selectivity of only 96,5% is achieved, falling to 92% after 150 hours. According to German Offenlegungsschrift No. 25 47 309, 2,4,6-trimethyl phenol is obtained in a yield of 95% by methylating p-cresol, 2,3,6-trimethyl phenol being obtained in a yield of 94% from m-cresol, whereas according to German Offenlegungsschrift No. 23 29 812, 2,3,6-trimethyl phenol is obtained in a yield of 82% from m-cresol.

SUMMARY OF THE INVENTION

According to the present invention, it has been found that phenols having at least one free o-position can be substituted in the o-positions by catalytic reaction with alcohols and/or their ethers by reacting phenol and/or mono- and/or di-alkyl phenols for 0.05 to 10 seconds with methanol and/or dimethyl ether in a molar ratio of 1:0.1–10 at a temperature of between 270° to 390° C. in the gas phase in the presence of a catalyst consisting of oxides of iron, chromium, silicon and at least one oxide of an alkaline-earth metal, lanthanum and manganese or in the presence of a catalyst consisting of oxides of iron, chromium, one or more oxides of germanium, titanium, zirconium, tin and lead and of at least one oxide of an alkali metal, alkaline-earth metal, lanthanum and manganese, the molar ratios of the components amounting to 100:0.1–10:0.1–10:0.1–10.

DESCRIPTION OF THE PREFERRED EMBODIMENTS

For alkylating phenol, mono- or di-alkyl phenols with alcohols and/or their ethers, the starting material or mixtures thereof are vaporised in the usual way and introduced in the ratio indicated into a reactor in which the catalyst is arranged, for example in the form of a fixed bed. The reaction may also be carried out with advantage in a fluidised bed in the process according to the invention. In addition, steam may be introduced with the starting products in such a quantity that the molar ratio of phenol and/or alkyl and di-alkyl phenol to steam amounts to about 1:1–5. The reactor is operated at a temperature in the range from 270° to 390° C. The reaction is generally carried out at normal pressure, although it may also be carried out with advantage under elevated pressure. Thus, it has been found for example that, where p-substituted phenols are used, equally good results are obtained even where pressures of up to around 30 bars are applied.

The catalyst used is, for example a mixture of iron oxide, chromium oxide, silicon oxide and alkaline-earth oxide in which iron oxide is present in excess.

The catalyst may also consist for example of a mixture of iron oxide, chromium oxide, one or more oxides of germanium, titanium, zirconium, tin and lead and at least one oxide of the First or Second Main Group of the Periodic System. The oxides of germanium, titanium, zirconium, barium, calcium, strontium and manganese are preferred.

The starting materials are used in such a quantity that a residence time of 0.01 to 10 seconds and preferably from 1 to 3.5 seconds is obtained.

After leaving the reactor, excess alcohol or ether is removed by distillation from the product mixture. The product mixture is then separated from the aqueous phase. Unreacted starting materials are distilled off and returned to the reactor.

The selectivity with which substitution takes place in the free o-positions generally amounts to 98–99%. Even after a production time of 2000 hours, there are still no signs of any significant reduction in the selectivity of the catalyst. A major advantage of the process according to the invention lies in the fact that the consumption of methanol is considerably lower than in conventional processes. The process according to the invention is illustrated by the following Examples:

EXAMPLE 1

A mixture of o-cresol and phenol, methanol and water in a molar ratio of 1 (o-cresol and phenol) to 4 (methanol) to 2.6 (water) was introduced in vapour form into a fixed-bed reactor heated to around 360° C. and containing a catalyst consisting of iron oxide, silicon oxide, chromium oxide and calcium oxide in a molar ratio of 100:2:1:0.2. The starting products were introduced under normal pressure in such a quantity that the residence time amounted to 3 seconds. The product leaving the reactor was cooled in countercurrent to the starting product. Excess methanol was distilled off from the condensate accumulating. The aqueous phase was separated off from the sump. The small quantity of o-cresol and phenol was distilled off from the organic phase, of which 99% consisted of 2,6-xylenol, and returned to the reactor. The 2,6-xylenol remaining in the sump, which still contained 0.5% of 2,4,6-trimethyl phenol, was subjected to fine distillation in another column.

The total yield of 2,6-xylenol, based on o-cresol and phenol, amounted to 99%. The 2,6-xylenol obtained overhead was 99.9% pure. After 2000 hours, the catalyst still showed a selectivity of 98,2%.

EXAMPLE 2

Phenol, dimethyl ether and water in a molar ratio of 1:2.5:2.5 were reacted in the vapour phase in the same way as described in Example 1. After working up, 2,6-xylenol was obtained with a selectivity of 99%.

EXAMPLE 3

Phenol, methanol and water in a molar ratio of 1:0.5:2.5 were reacted in the vapour phase in the same way as described in Example 1, except that the reaction temperature was 340° C. and the residence time 5 seconds.

o-cresol was obtained with a selectivity of 96% and 2,6-xylenol with a selectivity of 3.6%, based on the phenol reacted. Even after 2100 hours, the activity and selectivity of the catalyst showed only a negligible reduction.

EXAMPLE 4 o-cresol, methanol and water in a ratio of 1:2.5:2.5 were reacted in the same way as in Example 1. The catalyst contained iron oxide, titanium oxide, chromium oxide and calcium oxide in a molar ratio of 100:4,5:2:0,5. After working up, 2,6-xylenol was obtained with a selectivity of 99.1%.

EXAMPLE 5 m-cresol, methanol and water in a molar ratio of 1:5:2.5 were reacted in the same way as described in Example 1. The catalyst contained iron oxide, silicon oxide, chromium oxide and barium oxide in a molar ratio of 100:2:1:0,2. After working up, 2,3,6-trimethyl phenol was obtained with a selectivity of 99.5%.

EXAMPLE 6 p-cresol, methanol and water were used in a molar ratio of 1:5:1 and reacted in the gas phase over the catalyst described in Example 1 under a pressure of 20 bars. After working up, 2,4,6-trimethyl phenol was obtained with a selectivity of 99%.

EXAMPLE 7 p-cresol, methanol and water were reacted in a ratio of 1:0.5:0.5 in the same way as in Example 1. 2,4-xylenol was obtained with a selectivity of 96% and 2,4,6-trimethyl phenol with a selectivity of 3%.

EXAMPLE 8 o-cresol, methanol and water in a ratio of 1:2.5:2.5 were reacted in the same way as described in Example 1. The catalyst contained iron oxide, germanium oxide, chromium oxide and barium oxide in a ratio of 100:2:10:1. After working up, 2,6-xylenol was obtained with a selectivity of 99.2%.

EXAMPLE 9 o-cresol, methanol and water in a ratio of 1:2.5:2.5 were reacted in the same way as described in Example 1. The catalyst contained iron oxide, tin oxide, chromium oxide and calcium oxide in a molar ratio of 100:2:1:1. After working up, 2,6-xylenol was obtained with a selectivity of 98.9%. Even after 2000 hours, there was no change in the activity of selectivity of the catalyst.

EXAMPLE 10 m-cresol, methanol and water in a molar ratio of 1:5:2.5 were reacted in the same way as described in Example 1. The catalyst contained iron oxide, germanium oxide, chromium oxide and barium oxide in a molar ratio of 100:2:1:1. After working up, 2,3,6-trimethyl phenol was obtained with a selectivity of 99.2%.

EXAMPLE 11 p-cresol and methanol in a molar ratio of 1:5 were reacted in the same way as described in Example 1, but under a pressure of 5 bars. The catalyst contained iron oxide, zirconium oxide, chromium oxide and barium oxide in a molar ratio of 100:2:1:1. After working up, 2,4,6-trimethyl phenol was obtained with a selectivity of 99.2%.

EXAMPLE 12

Phenol, methanol and water in a ratio of 1:0.5:2.5 were reacted in the same way as described in Example 1, but at 330° C. The catalyst contained iron oxide, germanium oxide, chromium oxide and calcium oxide.

Working up showed that the phenol had reacted to form o-cresol with a selectivity of 95% and 2,6-xylenol with a selectivity of 4.5%. Less than 0.5% of secondary products were formed.

EXAMPLE 13

A mixture of o-cresol and phenol, methanol and water in a molar ratio of 1:4:2,6 was reacted in vapour form as described in Example 1.

The yield of 2,6-xylenol, based on o-cresol and phenol, amounted to 99,9%. The 2,6-xylenol obtained was 99,9% pure. After 2000 hours, the catalyst still showed a selectivity of 98,2%.

EXAMPLE 14 o-cresol, methanol and water in a molar ratio of 1:2,5:2,5 were reacted in the same way as in Example 1. The catalyst consisted of iron oxide, zirconium oxide, chromium oxide and lanthanium oxide in a molar ratio of 100:3:2:0,5.

After working up, 2,6-xylenol was obtained with a selectivity of 98,2%.

EXAMPLE 15 o-cresol, methanol and water in a molar ratio of 1:2,5:2,5 were reacted as described in Example 1. The catalyst contained iron oxide, tin oxide, chromium oxide and manganese oxide in a molar ratio of 100:2:1:1. After working up, 2,6-xylenol was obtained with a selectivity of 98,7%.

EXAMPLE 16 m-cresol, methanol and water in a molar ratio of 1:5:2,5 were reacted as described in Example 1. The catalyst contained iron oxide, germanium oxide, chromium oxide and lanthanium oxide in a molar ratio of 100:2:1:1. After working up, 2,3,6-trimethylphenol was obtained with a selectivity of 99%.

EXAMPLE 17 p-cresol and methanol in a molar ratio of 1:5 were reacted as described in Example 1, but under a pressure of 5 bars. The catalyst contained iron oxide, zirconium oxide, chromium oxide and manganese oxide in a molar ratio of 100:2:1:1. After working up, 2,4,6-trimethyl phenol was obtained with a selectivity of 99%.

EXAMPLE 18

Phenol, methanol and water in a molar ratio of 1:0,5:2,5 were reacted as described in Example 1, but at a temperature of 330° C.

o-cresol was obtained with a selectivity of 95% and 2,6-xylenol with a selectivity of 4,5%, based on the phenol reacted. The amount of secondary products was less than 0,5%.

What we claim is:

1. In a process for the production of ortho-methyl-substituted phenols by catalytically reacting phenols having at least one free o-position with methanol or dimethyl ether in the presence of a catalyst containing iron oxide and chromium oxide at an elevated temperature in the gas phase, the improvement which comprises reacting a compound selected from the group consisting of phenol, cresol, and xylenol for 0.05 to 10 seconds with methanol or dimethyl ether in a molar ratio of 1:0.1–10 at a temperature of between 270°–390° C. in the presence of a catalyst consisting of iron oxide, chromium oxide, silicon oxide and at least one oxide of a metal of the group consisting of alkaline earth metal, lanthanum and manganese, the molar ratio between the catalyst components being 100:0.1–10:0.1–10:0.01–10.

2. A process as claimed in claim 1 wherein o-cresol is reacted with methanol or dimethyl ether in a ratio of 1:0.5–5.

3. A process as claimed in claim 1 wherein a mixture of o-cresol and phenol is reacted.

4. A process as claimed in claim 1 wherein m-cresol is reacted.

5. A process as claimed in claim 1 wherein the reaction time is from 1 to 3.5 seconds.

6. In a process for the production of ortho-methyl-substituted phenols by catalytically reacting phenols having at least one free o-position with methanol or dimethyl ether in the presence of a catalyst containing iron oxide and chromium oxide at an elevated temperature in the gas phase, the improvement which comprises reacting a compound selected from the group consisting of phenol, cresol, and xylenol for 0.05 to 10 seconds with methanol or dimethyl ether in a molar ratio of 1:0.1–10 at a temperature of between 270°–390° C. in the presence of a catalyst consisting of iron oxide, chromium oxide, at least one oxide of a metal of the group consisting of germanium, titanium, zirconium, tin and lead and at least one oxide of a metal of the group consisting of alkali, alkaline earth, lanthanum and manganese, the molar ratio between the catalyst components being 100:0.1–10:0.1–10:0.01–10.

7. A process as claimed in claim 6 wherein o-cresol is reacted with methanol or dimethyl ether in a ratio of 1:0.5–5.

8. A process as claimed in claim 6 wherein a mixture of o-cresol and phenol is reacted.

9. A process as claimed in claim 6 wherein m-cresol is reacted.

10. A process as claimed in claim 6 wherein the reaction time is from 1 to 3.5 seconds.

* * * * *